(12) United States Patent
Fois et al.

(10) Patent No.: US 10,948,481 B2
(45) Date of Patent: Mar. 16, 2021

(54) DEVICE AND METHOD FOR DETERMINING THE ACTION OF ACTIVE INGREDIENTS ON NEMATODES AND OTHER ORGANISMS IN AQUEOUS TESTS

(71) Applicant: BAYER AKTIENGESELLSCHAFT, Leverkusen (DE)

(72) Inventors: Franco Fois, Monheim (DE); Michael Harnau, Leichlingen (DE); Klaus Ochmann, Leverkusen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/682,666

(22) Filed: Nov. 13, 2019

(65) Prior Publication Data

US 2020/0080992 A1    Mar. 12, 2020

Related U.S. Application Data

(62) Division of application No. 15/544,409, filed as application No. PCT/EP2016/050140 on Jan. 6, 2016, now Pat. No. 10,514,375.

(30) Foreign Application Priority Data

Jan. 23, 2015   (EP) .................................... 15152272

(51) Int. Cl.
G01N 33/50        (2006.01)
G01N 21/25        (2006.01)
(Continued)

(52) U.S. Cl.
CPC ....... *G01N 33/5085* (2013.01); *G01N 21/253* (2013.01); *G01N 21/255* (2013.01);
(Continued)

(58) Field of Classification Search
CPC . G06T 2207/30024; G06T 5/20; G06T 7/254; G06T 7/0012; G06T 2207/10056;
(Continued)

(56) References Cited

U.S. PATENT DOCUMENTS 4,660,969 A  *  4/1987  Sorimachi ................ G01C 3/10
                                                         356/3.01
6,129,437 A     10/2000  Koga et al.
(Continued)

FOREIGN PATENT DOCUMENTS

CN     103688275 A     3/2014
DE     19941167 A1     3/2000
(Continued)

OTHER PUBLICATIONS

Marcellino et al.,"WormAssap: A Novel Computer Application for Whole-Plate Motion Based Screening of Macroscopic Parasites" PLOS. (Jan. 2012) vol. 6, Issue 1, e1494:1-8.
(Continued)

*Primary Examiner* — Jingge Wu
(74) *Attorney, Agent, or Firm* — McBee Moore & Vanik IP, LLC

(57) ABSTRACT

The invention relates to a device (1) and a method for determining the action of active ingredients on nematodes and other organisms in aqueous tests. The device (1) according to the invention comprises a holder (13) for a cell culture plate (30) having multiple wells (31) in which the nematodes can be filled with the active ingredients, said cell culture plate (30) having a bottom side (33), a top side (32) and also side walls extending between bottom side (33) and top side (32), a camera (11) which is used to record images of preferably the bottom side (33) of the cell culture plate (30), a lighting mechanism (14) having at least a first light source (15) which illuminates the cell culture plate (30), there being
(Continued)

arranged between the first light source (15) and a first side wall (34) of the cell culture plate (30) in the installed state a first optical unit which directs the light of the first light source (15) through the first side wall (34) in the direction of the bottom side (33) of the cell culture plate (30). The method according to the invention makes it possible to simultaneously investigate many active ingredients within a very short time.

8 Claims, 4 Drawing Sheets

(51) Int. Cl.
  *G06T 7/254* (2017.01)
  *G06K 9/36* (2006.01)
  *G06T 5/20* (2006.01)
  *G06T 7/00* (2017.01)

(52) U.S. Cl.
  CPC ............ *G06K 9/36* (2013.01); *G06T 5/20* (2013.01); *G06T 7/0012* (2013.01); *G06T 7/254* (2017.01); *G01N 2201/0638* (2013.01); *G01N 2333/4353* (2013.01); *G06T 2207/30024* (2013.01)

(58) Field of Classification Search
  CPC ............ G01N 21/253; G01N 21/255; G01N 2201/0638; G01N 2333/4353; G01N 33/5085; G01N 15/1475; G01N 33/48; G01N 2201/0631
  See application file for complete search history.

(56) References Cited

U.S. PATENT DOCUMENTS

| | | |
|---|---|---|
| 6,211,953 B1 | 4/2001 | Niino et al. |
| 6,246,525 B1 | 6/2001 | Ikami |
| 2004/0233545 A1 | 11/2004 | Jiang |
| 2006/0194308 A1 | 8/2006 | Gutekunst et al. |
| 2008/0259328 A1 | 10/2008 | Hirano et al. |
| 2008/0266653 A1* | 10/2008 | Korpinen ............ G02B 21/26 359/368 |
| 2009/0135603 A1* | 5/2009 | Graessle ............ G01N 15/1475 362/293 |
| 2010/0184616 A1 | 7/2010 | Hillendahl et al. |
| 2011/0312102 A1 | 12/2011 | Jo et al. |
| 2012/0087143 A1 | 4/2012 | Hill et al. |
| 2012/0188786 A1 | 7/2012 | Burges et al. |
| 2013/0034272 A1 | 2/2013 | Thomas |
| 2014/0227774 A1 | 8/2014 | Guthrie et al. |
| 2018/0246127 A1* | 8/2018 | Bergmann ............ G01N 33/74 |

FOREIGN PATENT DOCUMENTS

| | | |
|---|---|---|
| EP | 0625569 A1 | 11/1994 |
| EP | 0926483 A2 | 6/1999 |
| EP | 1686368 A2 | 8/2006 |
| GB | 2479628 A | 10/2011 |
| WO | 94/05770 A1 | 3/1994 |
| WO | 2006107864 A1 | 10/2006 |

OTHER PUBLICATIONS

Marcellino et al., "Wormassay: A Novel Computer Application for Whole-Plate Motion-Based Screening of Macroscopic Parasites", plosntds.org (2012) VIL. 6, pp. 1-8.

* cited by examiner

DEVICE AND METHOD FOR DETERMINING THE ACTION OF ACTIVE INGREDIENTS ON NEMATODES AND OTHER ORGANISMS IN AQUEOUS TESTS

CROSS-REFERENCE TO RELATED APPLICATIONS

This application is a divisional of U.S. application Ser. No. 15/544,409, filed Jul. 18, 2017, which is a National Stage entry of International Application No. PCT/EP2016/050140 filed Jan. 6, 2016, which claims priority to European Patent Application No. 15152272.9, filed Jan. 23, 2015, the content of each of these applications is herein incorporated by reference in their entirety.

BACKGROUND OF THE INVENTION

Field of the Invention

The invention relates to a device and a method for determining the action of active ingredients on nematodes and other organisms in aqueous tests.

Description of Related Art

Many species of nematodes (roundworms) represent agricultural pests, since they can severely impair plant metabolism as a result of their penetration into the root systems. Various chemical substances, the so-called nematicides, have already been developed against an attack by nematodes. However, there is a great demand to identify further active ingredients which can control nematodes effectively.

A publication by Macellino, Gut et al. (Marcellino C, Gut J, Lim K C, Singh R, McKerrow J, et al. (2012) WormAssay: A Novel Computer Application for Whole-Plate Motion-based Screening of Macroscopic Parasites. PLoS Negl Trop Dis 6(1): e1494. doi:10.1371/journal.pntd.0001494) discloses a device for determining the action of active ingredients on worms, comprising a holder for a cell culture plate having multiple wells in which the worms can be filled with the active ingredients. Said cell culture plate has a bottom side, a top side and also side walls extending between bottom side and top side of the cell culture plate. The device further comprises a camera which is used to record images of the bottom side of the cell culture plate. A lighting mechanism of the device has at least one light source which illuminates the cell culture plate.

It has become apparent that disruptive influences such as condensed drops on a film cover of the cell culture plate can greatly influence the experimental results. A poorly adjusted lighting mechanism can lead to the experimental results being unusable.

SUMMARY

It is therefore an object of the invention to provide a device for determining the action of active ingredients on nematodes, which device can minimize the disruptive influences and thus allow a reliable determination of the action of the active ingredients.

The object underlying the invention is achieved by the combination of features according to claim 1. Exemplary embodiments of the invention can be gathered from claims 2 to 8.

According to claim 1, there is arranged between a first light source and a first side wall of the cell culture plate in the installed state a first optical unit which directs the light of the first light source through the first side wall in the direction of the bottom side of the cell culture plate. In one exemplary embodiment, the optical unit comprises a lens which directs and/or focuses the light of the first light source in the direction of the bottom side of the cell culture plate.

DETAILED DESCRIPTION OF A PREFERRED EMBODIMENT

The optical unit can have a rod lens which substantially spans the entire length of the first side wall of the cell culture plate. In this connection, the rod lens can spread out in parallel to the first side wall. A central axis of the rod lens is preferably between the plane of the top side of the cell culture plate and the plane of the bottom side of the cell culture plate.

The first light source can have a line light guide which preferably also spans the entire length of the first side wall of the cell culture plate. Thus, light is fed into the cell culture plate across the entire first side wall, the rod lens causing the light to be directed and/or focused in the direction of the bottom side of the cell culture plate. The line light guide or its central axis is preferably between the plane of the top side and the plane of the bottom side of the cell culture plate supported by the holder. In this connection, the beams of the light from the line light guide run substantially parallel to the top side or bottom side of the cell culture plate and then strike the rod lens, which then directs the light in the direction of the bottom side.

In one exemplary embodiment, the optical unit prevents a direct illumination of a top well-cover of the cell culture plate. Said top well-cover can, for example, be designed in the form of a film, on which condensation water can form. However, a disruptive influence of these condensed drops on the investigation results can be reduced or completely eliminated by the targeted illumination of the cell culture plate.

Alternatively or additionally, the optical unit can be designed such that a direct penetration of light into an objective of the camera is prevented. This, too, has been found to be necessary for the quality and reliability of the investigation results.

In one exemplary embodiment of the invention, a gap between the first light source and the rod lens is from 2 to 4 cm. Preferably, there is provided an adjustment mechanism which makes it possible to set the gap between light source and rod lens within certain limits in a freely selectable manner. In this connection, it is preferably possible by means of the adjustment mechanism to set not only the (horizontal) gap between light source and rod lens, but also a height offset between light source and rod lens.

In one exemplary embodiment, the holder is composed of a transparent material. Preferably, a thermoplastic such as PMMA (acrylic glass) is used.

The lighting mechanism can have a second light source and a second optical unit, which is arranged on a second side wall of the cell culture plate, said second side wall being opposite to the first side wall. In this connection, the second optical unit can be identical to the first optical unit. In addition, the arrangement of second light source in relation to the second optical unit can correspond to the arrangement as exists between first light source and first optical unit.

Owing to the multiplicity of active ingredients, the action of which is to be investigated on nematodes, there is a need to provide a method with the aid of the above-described device, which device makes it possible to investigate the active ingredients in the shortest possible time. It is therefore an additional object of the invention to provide a method for determining the action of active ingredients on nematodes, which method makes it possible to investigate as many active ingredients as possible in a short time.

This object is achieved by the method according to claim 9. Exemplary embodiments of the method according to the invention can be gathered from the claims dependent on claim 9.

The method according to the invention for determining the action of active ingredients on nematodes and other organisms in aqueous tests envisages firstly the filling of at least one well of a cell culture plate with nematodes and an active ingredient. The cell culture plate is then placed into a device according to the above designs. At this point, it should be pointed out that, alternatively, the cell culture plate can be arranged in a device differing from the designs according to claims 1 to 8.

Then, multiple digital images following one another chronologically are created of the cell culture plate, preferably from the bottom side. Said images are binarized, with each pixel of an image being assigned to a first group (e.g. "black") or a second group (e.g. "white"). In the binarization, a threshold value can be defined/established: a pixel, the intensity of which is less than said threshold value, belongs to the background, whereas a pixel, the intensity of which is greater than said threshold value, is assigned to the nematodes. In this connection, the level of the threshold value is dependent on the illumination of the cell culture plate and thus dependent on the lighting mechanism used.

Before the images are binarized, it is useful to use a morphological image processing filter. This involves filtering out objects, the size of which is greater than that of the organisms investigated. Accordingly, this process step requires an input size, which specifies the size of the organisms investigated.

After binarization, a first measurement curve is determined for a first series of recordings, said first measurement curve being based on the at least one well and thus on the active ingredient previously filled into said well. In this connection, the first series of recordings has a base image and multiple follow-up images, with each follow-up image being compared to the base image in a difference method and a number of difference pixels being determined in each case. Furthermore, at least a second measurement curve based on the well is determined for a second series of recordings, and, for the second series, a follow-up image of the first series is used as base image and at least one further follow-up image of the first series is used as a follow-up image of the second series. Lastly, an averaged curve is determined on the basis of the first measurement curve and of the at least second measurement curve.

Because an individual image is used for various measurement curves, it is possible to minimize the number of images to be recorded and thus the time required therefor. Owing to the creation of multiple measurement curves, which are then included in an averaged curve, it is possible to reduce the statistical variance or scattering to the extent that it is possible on the basis of the averaged curve to provide reproducible and reliable first information about the action of the active ingredient.

In one design of the invention, what is used for the base image of the second series is a first follow-up image of the first series, which first follow-up image immediately follows the base image of the first series (i.e. there are no images which are recorded in the interim). Furthermore, what are used for the second series are all follow-up images of the first series as follow-up images of the second series, except for the first follow-up image of the first series. The second series then merely has to be completed by an additional follow-up image. For example, if the first series consists of one base image and 9 follow-up images, the 9 follow-up images of the first series are used for the second series, with the first follow-up image of the first series being used as base image of the second series and the remaining 8 follow-up images of the first series all being used as follow-up images of the second series. So that the second series likewise has 9 follow-up images, said second series must be completed by an additional image. Thus, altogether 11 images following one another chronologically are sufficient for creating the first measurement curve and the second measurement curve, each containing 10 points (including zero point) which represent the number of difference pixels at different times.

A recording period between the base image and the last follow-up image of a series can be established such that, within said recording period, an asymptotic limit is reached for the number of difference pixels for a well in which untreated nematodes are situated. The background to the asymptotic limit shall be elucidated using the example of a well in which—for simplification—merely only one roundworm has been filled:

If, for example, 50 white pixels can be assigned to this individual roundworm, the maximum number of difference pixels arising from a comparison of a base image (at time t=0) with a subsequently following follow-up image is 100. The number 100 arises when the roundworm has completely moved out of its original position (time t=0). Firstly, the original 50 white pixels of the roundworm are now black. Secondly, 50 other pixels, which were previously black, are now white due to the new position of the roundworm. If said roundworm then moves further, the number of difference pixels remains constant, however. In this simplistic model, the recording period thus corresponds to the time required by an untreated roundworm to completely move from its original position (defined by the base image). Preferably, 50 to 100 nematodes are generally filled into a well, and so the asymptotic value does not necessarily have to correspond to twice the pixels classified as "white". However, it becomes apparent that the number of difference pixels runs against an asymptotic limit.

A total period can be established between the base image of the first series and a last follow-up image of a last series, which total period can approximately correspond to twice that of a recording period (for example within a range between 1.5 and 2.5).

The time interval between two successive images can be constant in each case and be from 1 to 5 seconds. One series of images can comprise from 8 to 12 images. The averaged curve can be determined on the basis of from 8 to 12 measurement curves.

If, for example, a recording period of 30 seconds, in which the asymptotic limit is reached, is determined for a well containing untreated nematodes, the total period can be 60 seconds. An interval of three seconds between two images following one another chronologically thus yields, for one recording period, a number of 11 images per series (one base image and 10 follow-up images, the base image being recorded at time t=0). A total period of 60 seconds, in which the first image is recorded at time t=0 and the last image is recorded at time t=60 seconds, thus yields altogether 21 images, which then yield 11 measurement curves, each containing 11 measurement points (including zero point).

The invention shall be more particularly elucidated on the basis of the exemplary embodiments depicted in the figures, in which.

Figure 1:
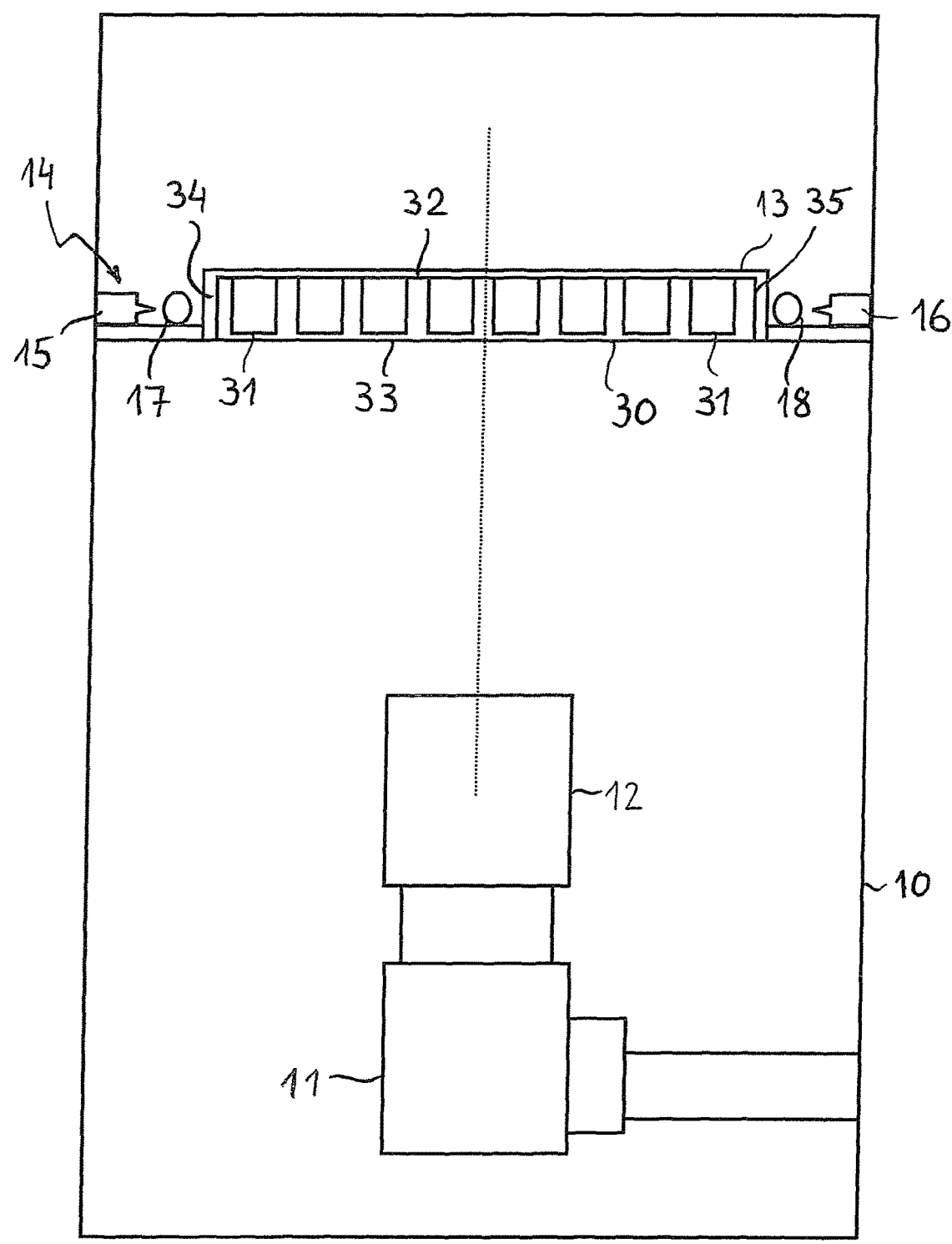
FIG. 1 shows schematically in cross section one exemplary embodiment of the device according to the invention.

FIG. 1 shows schematically in cross section a device for determining the action of active ingredients on nematodes. The device 1 has a housing 10, in which a camera 11 having an objective 12 is arranged. Furthermore, the housing 10 is provided with a holder 13 for a cell culture plate 30 which comprises multiple wells 31. The cell culture plate 30 has a top side 32 and a bottom side 33. Arranged between the top side 32 and the bottom side 33 of the rectangular cell culture plate 30 are four side walls, of which a first side wall 34 and an opposing second side wall 35 can be recognized in the depiction in FIG. 1.

A lighting mechanism 14 having a first light source 15 and a second light source 16 is likewise arranged in the housing 10. Arranged between the first light source 15 and the first side wall 34 is, as part of a first optical unit, a rod lens 17, which, like the first light source 15, spans the entire length of the first side wall 34. A rod lens 18 is arranged too between the second light source 16 and the second side wall 35.

The device 10 makes it possible, using the camera 11, to create multiple digital images of the cell culture plate 30 that follow one another chronologically, the images being recorded from the bottom side 33 of the cell culture plate 30. Accordingly, the camera 11 with its objective 12 is arranged below the holder 13 for the cell culture plate 30. Here, the device 10 has means, which are not further depicted, for storing and for processing the images recorded by the camera 11. Alternatively, the device 10 can be connected to appropriate (computer) means.

Figure 2:
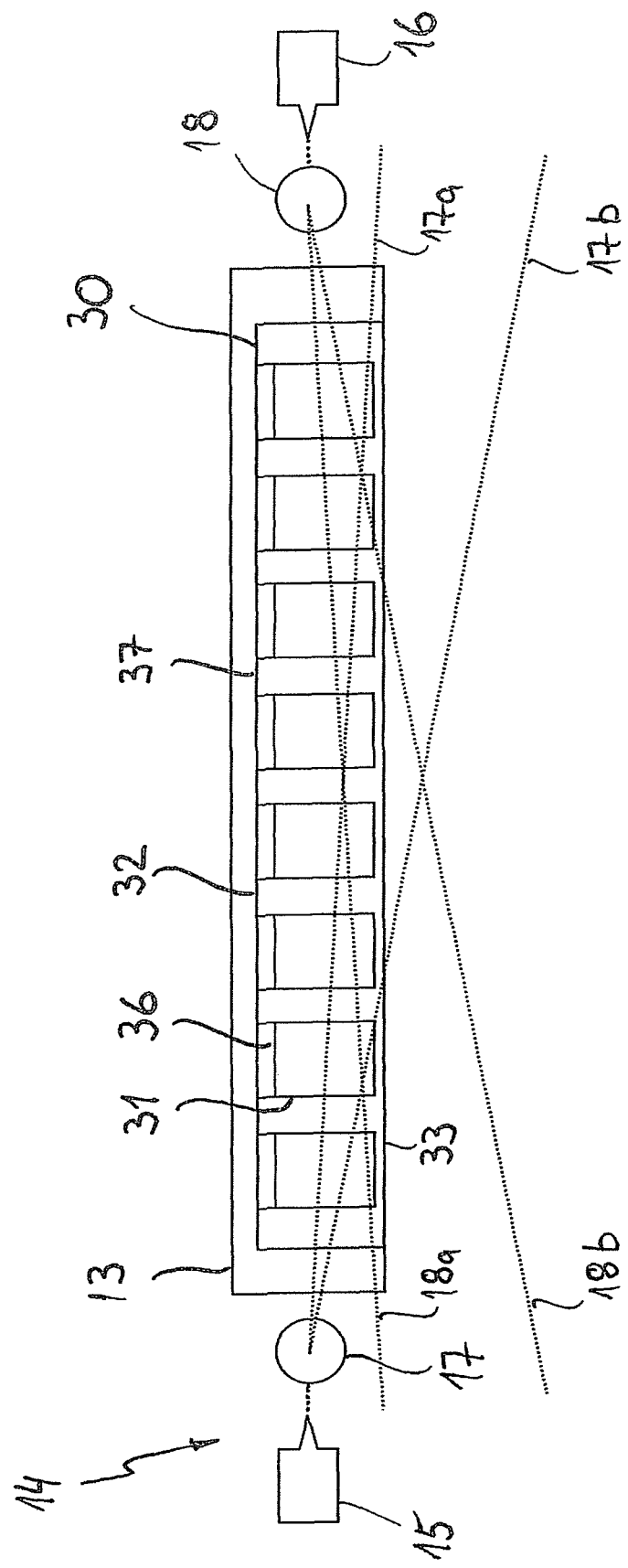
FIG. 2 shows schematically the arrangement of a cell culture plate and a lighting mechanism of the device according to FIG. 1.

FIG. 2 shows, on an enlarged scale, the arrangement of the cell culture plate 30 and the lighting mechanism 14 having the first light source 15 and the second light source 16. The individual wells 31 of the cell culture plate 30 are filled with an aqueous solution 36 in which from 50 to 100 nematodes and an active ingredient to be investigated are situated. FIG. 2 depicts eight wells 31 arranged in a row, and twelve rows arranged next to one another would give altogether 96 individual wells 31. Other patterns for the cell culture plate 30 are possible, for example a 4×6 pattern or 6×8 pattern.

Different active ingredients can be filled into the different wells 31. In addition, there can also be wells in which only nematodes without active ingredient are situated in the aqueous solution.

The rod lenses 17, 18 cause the light of the light sources 15, 16 to be directed in the direction of the bottom side 33. At the same time, the rod lenses 17, 18 prevent the light of the light sources 15, 16 from directly reaching the top side 32 of the cell culture plate 30, there being provided on the top side 32 a film 37 which covers the individual wells 31 from above. In addition, the rod lenses 17, 18 or the arrangement of the rod lenses 17, 18 are designed such that no light directly falls into the objective 12 of the camera 11.

17a and 17b indicate light beams emerging from the rod lens 17. Corresponding exit beams of the rod lens 18 are indicated by 18a, 18b.

FIG. 2 reveals that the rod lenses 17, 18, at least the central axes thereof extending perpendicularly to the drawing plane, are arranged between the top side 32 and the bottom side 33 of the cell culture plate 30 when the cell culture plate 30 is situated in the holder 13 of the device 10, which holder 13 is intended for said cell culture plate 30.

Figure 3:
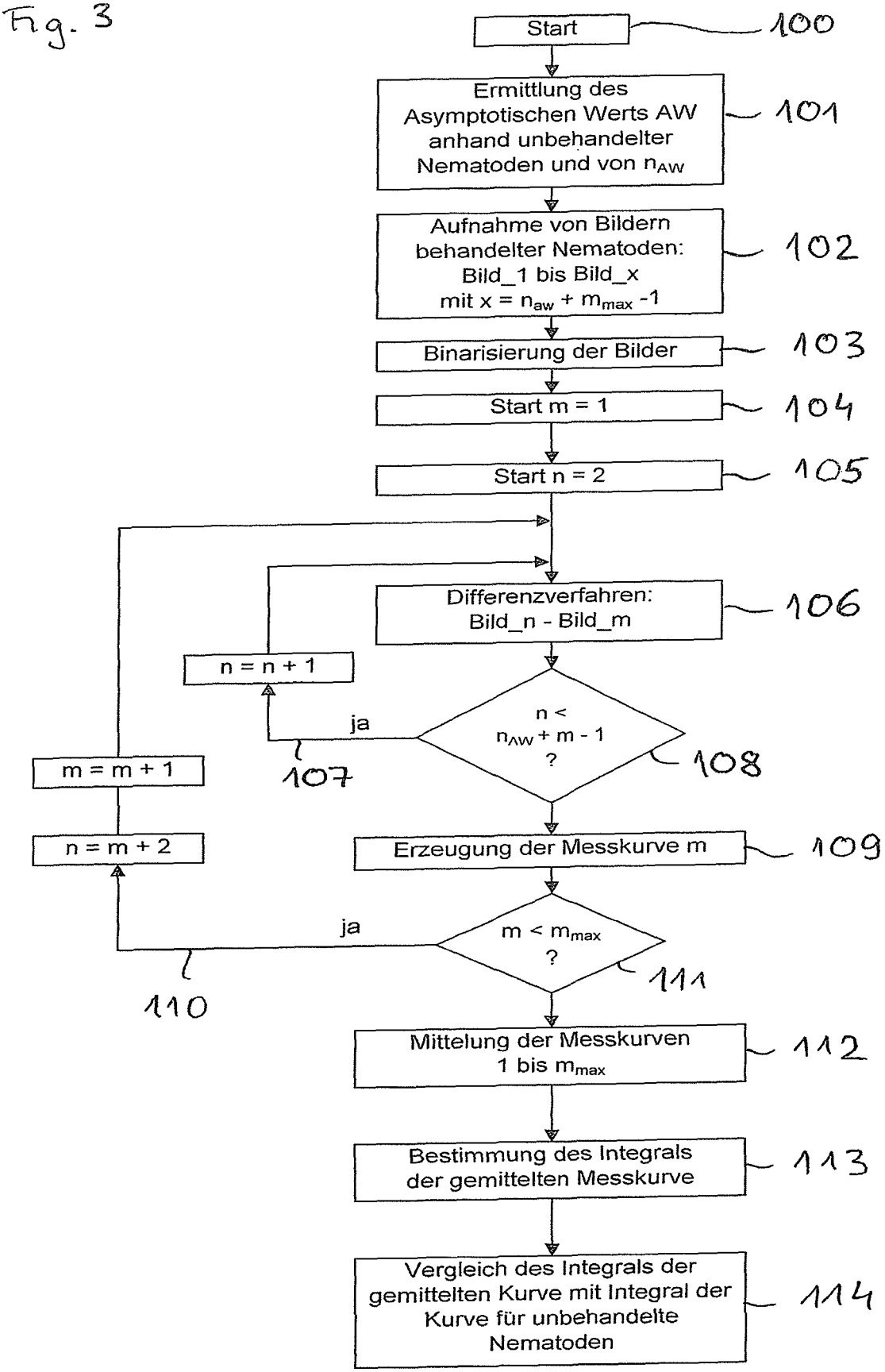
FIG. 3 shows a flow chart of one exemplary embodiment of the method according to the invention.
Figure 4:
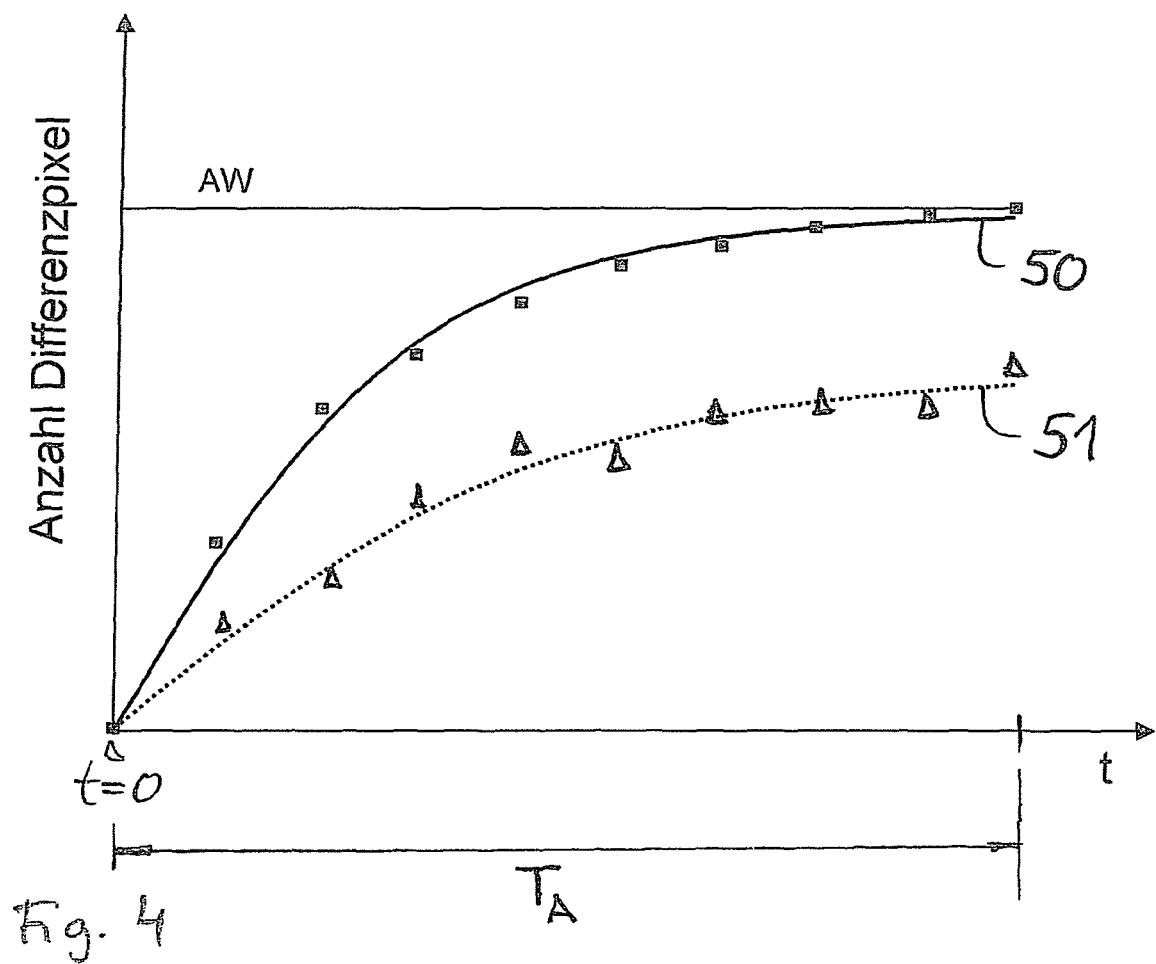
FIG. 4 shows a measurement curve for a well containing untreated nematodes and a measurement curve for nematodes treated with an active ingredient.

FIG. 3 shows a flow chart of one exemplary embodiment of the method according to the invention. The flow chart starts with a start block 100. In block 101, an asymptotic value AW is determined on the basis of untreated nematodes. In this connection, the asymptotic value AW is the number of difference pixels which can maximally arise when a follow-up image is compared with a base image. FIG. 4 shows such an asymptotic value AW for a measurement curve 50 for untreated nematodes. In this connection, the individual measurement points reflect the number of difference pixels arising in the comparison of the follow-up images recorded at different times with a base image recorded at time t=0. In this connection, the asymptotic value AW is linked to a recording period $T_A$, within which the measurement curve 50 at least approximately reaches the asymptotic limit AW. In the present example, the recording period shall be 27 seconds, and the interval between two adjacent follow-up images or the interval between the first follow-up image and the base image (t=0) shall be three seconds. Therefore, a number $n_{AW}$ of images per measurement curve including the base image (t=0) is equal to 10.

FIG. 4 also shows exemplarily an (averaged) measurement curve 51 for treated nematodes. What can be seen is that the measurement curve 51 runs below the measurement curve 50 for the untreated nematodes, since the treated nematodes move more slowly or some of them no longer move. The smaller the area under the measurement curve 51 with regard to the area below the measurement curve for untreated nematodes, the stronger the action of the corresponding active ingredient. The averaged measurement curve 51 will, however, be discussed in more detail later on.

After the determination of the asymptotic value AW on the basis of untreated nematodes and after the establishment of the number of images $n_{AW}$ per measurement curve or per series (block 101), what then takes place is, according to FIG. 3 in block 102, the recording of a certain number of images Image_1 to Image_x. At this point, it should be pointed out that the camera 11 creates at each time a total image of the cell culture plate 30 with all wells, and the images Image_1 to Image_x are then cut out or created for each individual well from said total image in a well-based manner. Said images are then binarized in block 103. In the binarization, the individual pixels are assigned either to the nematodes (white pixel) or to the background (black pixel). The binarization in block 103 must take place downstream of an establishment of a threshold value for the intensity of the pixel, which value makes it possible to divide the pixels into "white" and "black".

For a first measurement curve m=1 (see block 104), the images Image_2 to Image_$n_{AW}$ are then used, in that the number of difference pixels between initially a first follow-up image Image_2 and the base image Image_1 is determined by means of a difference method (see block 105 and block 106). In this connection, block 106 is passed through multiple times as part of a loop, and so the number of difference pixels is determined for multiple follow-up images (Image_2–Image_1; Image_3–Image_1; Image_4–Image_1; ...; Image_$n_{AW}$–Image_1). The loop 107 is exited when the number of images for the first measurement curve has reached the value $n=n_{AW}+m-1$ and the query 108 provided within the loop 107 cannot be answered with "Yes". In this case, all values are available for creating the first measurement curve m=1 (cf. block 109).

After creation of the first measurement curve m=1, the loop 110 is then used to create further measurement curves (m=2, m=3, . . . , $m=m_{max}$). In this connection, a second measurement curve is based on the difference images Image_3−Image_2; Image_4−Image_2; . . . ; $Image\_n_{AW}+1$−Image_2. Therefore, Image_3, for example, is used both for the creation of the first measurement curve m=1 and for the second measurement curve m=2.

When a query 111 within the loop 110 cannot be answered with "Yes", the loop 110 is exited. All measurement curves 1, 2, . . . , $m_{max}$ are now available, and so these measurement series can be averaged in block 112. It has been found that this averaging of the individual measurement series, which rely on the same images for the most part, can considerably reduce the statistical scattering. Thus, it is possible using altogether $m+n_{AW}-1$ images to generate m measurement series, each containing $n_{AW}$ measurement points (including the zero point).

In block 113, the integral of the averaged curve is calculated, and said integral can then be compared with the area under the measurement curve 50 for untreated nematodes (see block 114).

Assuming that the measurement series 51 already mentioned above in FIG. 4 corresponds to the averaged measurement series according to block 112 and that the area below the measurement curve 50 comprises $I_{50}=100$ area units and the area below the (averaged) measurement curve comprises $I_{51}=65$ area units, it is possible to provide information about the efficacy of the active ingredient in accordance with the following formula: $(I_{50(untreated)}-I_{51(treated)})/I_{50(untreated)} \cdot 100\%$. In the case of the number example taken as a basis here, a value of 35% would then arise.

Thus, it is, for example, possible in the case of a cell culture plate having 96 wells to investigate almost 100 active ingredients at the same time. 60 seconds are sometimes enough for the recording of the images required for generating a sufficient number of measurement series with sufficient measurement points in order to achieve statistically reliable results. The invention therefore allows a rapid and efficient investigation of the efficacy of active ingredients on nematodes or similar organisms.

LIST OF REFERENCE SIGNS

1 Device
10 Housing
11 Camera
12 Objective
13 Holder
14 Lighting mechanism
15 First light source
16 Second light source
17 Rod lens (17a, 17b exit beams)
18 Rod lens (18a, 18b exit beams)
30 Cell culture plate
31 Well
32 Top side
33 Bottom side
34 First side wall
35 Second side wall
36 Solution
37 Well-cover
100 Start block
101 Block
102 Block
103 Block
104 Block
105 Block
106 Block
107 Loop
108 Query
109 Block
110 Loop
111 Query
112 Block
113 Block
114 Block

The invention claimed is:

1. Method for determining the action of active ingredients on nematodes and other organisms in aqueous tests, comprising:
   a) filling at least one well of a cell culture plate with nematodes and an active ingredient;
   b) arranging the cell culture plate in a device comprising:
      i. a holder for the cell culture plate having multiple wells in which nematodes can be filled with active ingredients, said cell culture plate having a bottom side, a top side and also side walls extending between bottom side and top side;
      ii. a camera which is used to record images of optionally the bottom side of the cell culture plate;
      iii. a lighting mechanism having at least a first light source which illuminates the cell culture plate;
         there being arranged between the first light source and a first side wall of the cell culture plate in an installed state a first optical unit for directing the light of the first light source—through the first side wall in the direction of the bottom side of the cell culture plate;
   c) creating multiple images of the cell culture plate that follow one another chronologically;
   d) binarizing the created images depending on an illumination of the cell culture plate;
   e) determining a first measurement curve based on the well for a first series of images, said first series having a base image and multiple follow-up images, with each follow-up image being compared to the base image in a difference method and a number of difference pixels being determined;
   f) determining at least a second measurement curve based on the well for a second series of images, and, for the second series, using a follow-up image of the first series as base image and at least one further follow-up image of the first series as a follow-up image of the second series;
   g) determining an averaged curve on the basis of the first measurement curve and of the at least second measurement curve.

2. Method according to claim 1, wherein what is used for the base image of the second series is a first follow-up image of the first series, which first follow-up image immediately follows the base image of the first series, in that what are used for the second series are all follow-up images of the first series as follow-up images of the second series, except for the first follow-up image of the first series, and in that the second series is completed by an additional follow-up image.

3. Method according to claim 1, wherein a recording period ($T_A$) between the base image and the last follow-up image of a series is established such that, within said recording period ($T_A$), an asymptotic limit AW is reached for the number of difference pixels for a well in which untreated nematodes are situated.

4. Method according to claim 3, wherein a total period is established between the base image of the first series and a last follow-up image of a last series, which total period approximately corresponds to twice that of a recording period ($T_A$).

5. Method according to claim 1, wherein the time interval between two successive images is constant and is from 1 to 5 seconds.

6. Method according to claim 1, wherein one series of images comprises from 8 to 12 images.

7. Method according to claim 2, wherein the averaged curve is determined on the basis of from 8 to 12 measurement curves.

8. Method according to claim 1, wherein the lighting mechanism has a second light source and a second optical unit for directing the light of the second light source through a second side wall of the cell culture plate in the direction of the bottom side of the cell culture plate, said second side wall being opposite to the first side wall.

\* \* \* \* \*